United States Patent
Prescott et al.

(10) Patent No.: US 7,364,875 B2
(45) Date of Patent: Apr. 29, 2008

(54) METHOD FOR PRODUCING MEDICAL AND COMMERCIAL GRADE POLY-GAMMA-GLUTAMIC ACID OF HIGH MOLECULAR WEIGHT

(75) Inventors: Albert G. Prescott, Westford, MA (US); Louis R. Stock, II, Worcester, MA (US)

(73) Assignee: Cresent Innovations, Inc., Westford, MA (US)

( * ) Notice: Subject to any disclaimer, the term of this patent is extended or adjusted under 35 U.S.C. 154(b) by 372 days.

(21) Appl. No.: 10/974,442

(22) Filed: Oct. 27, 2004

(65) Prior Publication Data

US 2005/0095679 A1 May 5, 2005

Related U.S. Application Data

(60) Provisional application No. 60/590,727, filed on Jul. 23, 2004, provisional application No. 60/515,879, filed on Oct. 30, 2003.

(51) Int. Cl.
*C12P 21/06* (2006.01)
*C12P 13/04* (2006.01)
*C12P 13/14* (2006.01)
*C12N 1/20* (2006.01)

(52) U.S. Cl. .................... 435/68.1; 435/69.1; 435/106; 435/110; 435/252.31; 435/252.5

(58) Field of Classification Search ............... 435/68.1, 435/69.1, 106, 110, 252.31, 252.5
See application file for complete search history.

(56) References Cited

U.S. PATENT DOCUMENTS 6,533,938 B1 * 3/2003 Dilorio et al. .............. 210/651

OTHER PUBLICATIONS

Louis Richard Stock II, Theological Characterization Of (Poly-y) Glutamic Acid Fermentations, Aug. 1996, 92 pages.
K. Kimura and Y. Itoh, *Appl. Environ. Microbiol.*, 69:2491-2497. 2003.
F.A. Troy. *J. Biol. Chem.* 248: 316-324. 1973.
F.A. Troy. *J. Biol. Chem.* 248: 305-315. 1973.
L.R. Stock. "Mixing and mass transfer studies of the fermentation product (poly)-y-glutamic acid." Ph.D. Dissertation, Worcester Polytechnic Institute. pp. 1-115. 2000.

* cited by examiner

*Primary Examiner*—Herbert J. Lilling
(74) *Attorney, Agent, or Firm*—Brian M. Dingman; Mirick, O'Connell, DeMollie & Lougene, LLP; Kerri P. Schray

(57) ABSTRACT

Methods for producing high molecular weight poly-gamma-glutamic acid (PGA). The PGA is produced by fermentation, and purified by use of tangential flow filtration, followed by diafiltration, as necessary, to yield a product of the desired purity. Product obtained may be of very high purity using all the prescribed purification steps. Product of this purity is suitable for in vivo medical applications. Other applications, such as food or agricultural, may utilize lower purity levels, and hence do not require all the purification steps specified.

20 Claims, No Drawings

METHOD FOR PRODUCING MEDICAL AND COMMERCIAL GRADE POLY-GAMMA-GLUTAMIC ACID OF HIGH MOLECULAR WEIGHT

CROSS-REFERENCE TO RELATED APPLICATIONS

This application claims priority of provisional application Ser. No. 60/515,879, filed on Oct. 30, 2003, and of provisional application Ser. No. 60/590,727, filed on Jul. 23, 2004.

FIELD OF THE INVENTION

This invention relates to methods for producing both medical and commercial grade poly-gamma-glutamic acid of high molecular weight.

BACKGROUND OF THE INVENTION

Poly-gamma-glutamic acid (also known as polyglutamate and PGA) is a biological polymer whose molecular weight can vary anywhere from 20,000 daltons to over 2 million depending on the method of production. PGA is a highly anionic homo-polyamid, whose only components are D- and L-glutamic acid. PGA forms elongated polymer chains through the formation of bonds at the alpha-amino and gamma-carboxylic acid groups. PGA is water soluble, biodegradable, edible and non-toxic toward humans. It is a major component of "natto", a traditional fermented soybean food in Japan.

PGA was first discovered and reported in 1937 by Ivanovics and co-workers who observed it released upon the cell lysis of *Bacillus anthracis*. In 1942, Bovarnick reported that *Bacillus subtilis* secreted PGA into its growth media. Various other *Bacillus* species were also found to produce PGA externally when fermented. The majority of these findings were published starting in the 1980's and early 1990's.

PGA has a very high negative charge density. The un-ionized form of the molecule adopts the configuration of a helix, whereas the ionized version maintains a random coil configuration.

PGA has been slow to find commercial application. There are several reasons for this. First, it was discovered in a dangerous human pathogen. Second, though glutamic acid is native to humans, poly-alpha-glutamic acid is not. Poly-alpha-glutamic acid is one of two possible isomers and is formed when PGA is manufactured by synthetic means. Poly-alpha-glutamic acid is the most common type of PGA available commercially. Poly-gamma-glutamic acid is the natural form of PGA. It is rare and commercially available from South Korea and Taiwan, but only in low molecular weight and low quality (i.e., not both high molecular weight and medical grade).

Several applications of PGA include environmental/industrial, agricultural, food, and pharmaceutical. One environmental application of PGA is its use as a flocculent. Another newer environmental application of PGA is in removing heavy metal contaminants, such as those used by the plating industry. As mentioned previously, PGA has a very large anionic charge density. Contaminants such as copper, lead, mercury and other positively-charged metal ions associate very strongly with PGA, and can then be concentrated and removed from the waste stream.

Since PGA is comprised of an amino acid, it is an excellent source of nitrogen. This suggests an application in agriculture as a fertilizer. For analogous reasons it is good for drug delivery. A polymer mixture can be packed with nutrients for a particular crop. Once the fertilizer is applied, it has a longer residence time in the soil since the fertilizer nutrients are protected from the natural environment by the PGA.

In the food industry, work has been done that shows PGA functions as a cryoprotectant. PGA has been shown to have antifreeze activity significantly higher than glucose, a common cryoprotectant. It has also been used as a stabilizer in ice cream and as a thickener in juice.

In the medical field, PGA is being studied as a biological adhesive and a drug delivery system. Gelatine-PGA solutions, and cross-linked PGA solutions have shown application as adhesives without the toxic or inflammatory issues. PGA has also been used in drug delivery. Taxol®, a well know cancer drug by Bristol-Myers Squibb, was covalently linked to PGA. The resulting molecule, (PG-TXL) in pre-clinical testing, showed a five-fold increase in tumor uptake of Taxol®.

Large MW PGA has advantages over low MW PGA including higher charge densities and higher viscosities at lower concentrations. This means that high molecular weight PGA would have advantages, including (1) greater reactivity with alkaline materials to make soap and other consumer products, of which the high viscosity is a required property, (2) more nitrogen delivered making it very useful in agriculture, (3) higher drug loading at the active negative sites, and (4) higher viscosities resulting in better drug diffusion properties.

The ability to deliver high MW PGA of the correct purity for the application is key.

Lastly, there is the issue of molecular weight and how it is measured. Several groups claim to have or produce high molecular weight gamma isomer PGA (claims range from 1 to 4 million). In general, these groups are using analytical methods not suited to PGA analysis. Most groups utilize size exclusion chromatography at neutral pH and physiological ionic strength. Under these conditions, PGA interacts with commercial columns, shifting peak retention times and giving erroneous results. In addition, these retention times must be compared to standards, which are typically non-ionic polymers. These standards do not have the same radius of gyration and thus do not behave like PGA, therefore results are typically incorrect.

In order to properly determine the molecular weight of PGA, one may employ an analytical method that involves low pH and low ionic strength, and couples size exclusion chromatography with multi-angle laser scattering, as described in a Master's Thesis By Louis R. Stock II entitled "Rheological Characterization of (Poly-γ) Glutamic Acid Fermentations" (1996) (incorporated herein by reference). Under these conditions, with the anionic sites fully protonated, PGA molecular weights may be correctly determined. Analysis under these conditions has established that the molecular weights of samples reported to be 1-4 million are in fact 25,000 to 400,000. There is thus a need for an economical, practical method of producing PGA at both low and high molecular weights with purities appropriate for both human and non-human uses.

SUMMARY OF THE INVENTION

Given the state of the art, there is a definite need for a novel method of producing PGA that is cost effective, capable of producing up to high molecular weight PGA, and does so at purity levels acceptable for commercial, agricultural, food, and medical uses. This invention relates to poly-gamma-glutamic acid that is either high or low molecular weight, and having a purity up to pharmaceutical grade.

It is an object of this invention to accomplish PGA production methods that allow one to produce lower molecular weight PGA at purities up to and including pharmaceutical, as well as high molecular weight (typical molecular weights are in the range of about 50,000 to about 4 million, with a molecular weight of about one million, with a polydispersity of about 1.1 to 1.2, being typical) PGA at any level of purity, up to and including pharmaceutical grade.

The invention features a method for producing high molecular weight poly-gamma-glutamic acid via the fermentation of a non-pathogenic organism. This PGA may be isolated and purified via a series of membrane filtration steps and/or pH adjustment and centrifugation. Inclusion of all steps results in a medical grade product capable of being used in vivo without any immune response from the body. If lower levels of purity are required, they may be achieved by selectively eliminating various purification steps. Purification is accomplished by buffer exchange via diafiltration using a filter with a molecular weight cutoff of less than about 100 kDa, and preferably at least about 30 kDa. Typically, in order to produce agricultural-grade PGA, viable cells are removed by filtration at about 0.22 microns. For a food-grade product, this would be followed by filtration at about 0.1 microns, which clarifies the product. Any medical use requires the diafiltration steps.

DETAILED DESCRIPTION OF THE PREFERRED EMBODIMENTS

The following is a description of the preferred embodiments of the invention. Organisms may include *Bacillus subtilus*, or recombinant *E. coli*, though *Bacillus licheniformis* ATCC 9945a is preferred. Any bacteria that produces PGA, including other strains of *Bacillus licheniformis*, may be used.

The organism is grown in a growth medium called "Medium E" that comprises glutamic acid, citric acid, glycerol, ammonium sulfate, dipotassium phosphate, magnesium sulfate, manganese sulfate, and calcium chloride. The fermentation is carried out at 37 C., agitated between 250-500 RPMs, and uses airflow of about 1 reactor volume per minute. It is preferred that the reactor be pressurized to increase the amount of dissolved oxygen. Fermentation time can vary from 3-5 days, but should be terminated when the broth viscosity ceases to substantially increase. The fermentation may be terminated by lowering the pH to about 2, or by simply moving to the purification cycle.

Upon completion, the fermentation broth is buffer exchanged via diafiltration using a filter with a molecular weight cut off (MWCO) of less than 100 kDa, and preferably about 30-100 kDa. The mixture of cells and PGA is then buffered in citric acid, and micro-filtered using a filter with an opening of 0.22 microns, and preferably less, to separate the PGA from the host cells.

The filtrate (which now contains the PGA and no host cells), is neutralized, and buffer exchanged and concentrated to the conditions desired using diafiltration and a filter with a MWCO of <100 kDa, and preferably about 30-100 kDa. Material from this purification may be sterile filtered, dried, freeze dried, precipitated in alcohol and/or refrigerated. Material from this stage is non-pyrogenic and may be injected in vivo without causing inflammation or an immune system response.

The following are examples of the invention.

EXAMPLE 1

PGA using Preferred Fermentation Method, and Purification to Medical Grade

*Bacillus licheniformis* ATCC 9945a was grown in Medium E. The fermentation was carried out at small scale, in shake flasks, at 37 C. Aeration was provided by diffusion. When the viscosity stopped rising (typically after about 3-5 days of fermentation), the fermentation broth was buffer exchanged via diafiltration using a filter with a molecular weight cut off (MWCO) of 30 kDa. The mixture of cells and PGA was then buffered in citric acid, and micro-filtered using a filter with an opening of 0.22 microns, to remove the host cells.

The filtrate was neutralized, and buffer exchanged with pure water and concentrated via diafiltration using a filter with a MWCO of 30 kDa. Material from this purification may be sterile filtered.

To describe the process in more detail, when the viscosity stopped rising, the fermentation broth was re-circulated through an Omega Polyethersulfon ultra-filtration cartridge by Pall Corporation with a 0.2 micron pore size. Once collected, the filtrate was re-circulated using an Omega Polyethersulfon ultra-filtration cartridge by Pall Corporation with a 0.16 micron pore size. The filtrate was collected and re-circulated through an Omega Polyethersulfon ultra-filtration cartridge by Pall Corporation with a 30 kDa MWCO pore size. Five diafiltration volumes of solution were processed. At the end, the retentate was collected, sterilized by passing through a 0.22 micron filter, and precipitated in sterile ethanol and stored.

Material from this example has been used in rats in subsequent experiments with no inflammatory response. The molecular weight was determined to be 2 million daltons using the following analytical MALLS method described in the Stock thesis that is incorporated by reference herein. PGA was dissolved at a concentration of 1 mg/ml in 0.1M citric acid, pH 2 to 3, with 0.05% sodium azide. The sample was degassed and 0.2 milliliters was injected at a flow rate of 0.5 mls/min. The SEC can utilize a TossoHaas TSK G5000PWXL, G6000PWXL, Waters Ultrahydrogel 1000 or 250. A Dawn DSP laser photometer from Wyatt technologies in conjunction with a Waters differential refractometer is used for detection.

This process is capable of making high molecular weight (when measured as described) poly-gamma-glutamic acid at purities up to and including pharmaceutical grade.

EXAMPLE 2

PGA From Another Commercial Source Purified

A sample reported to be poly-gamma-glutamic acid in excess of 1 million daltons was received from an offshore commercial supplier. The viscosity of a sample of known concentration seemed to be lower than would be the case if the PGA was indeed of the reported molecular weight. Analysis was impossible due to the large amount of contaminants, as evidenced by the off-white color noted when the sample was hydrated, and the fact that the hydrated sample had an odor similar to fermentation broth.

This material was re-circulated through an Omega Polyethersulfon ultra-filtration cartridge by Pall Corporation with a 0.2 micron pore size. Once collected, the filtrate was re-circulated using an Omega Polyethersulfon ultra-filtration cartridge by Pall Corporation with a 0.16 micron pore size. The filtrate was collected and re-circulated through an Omega Polyethersulfon ultra-filtration cartridge by Pall Corporation with a 30 kda MWCO pore size. Five diafiltration volumes of solution were processed. The resulting material was clear and odorless, supporting the production of low molecular weight, high purity PGA.

EXAMPLE 3

PGA

Bacillus licheniformis ATCC 9945a was grown in Medium E. The fermentation was carried out at small scale, in shake flasks, at 37 C. Aeration was provided by diffusion. When the viscosity stopped rising, the fermentation broth was buffer exchanged via diafiltration using a filter with a molecular weight cut off (MWCO) of 30 kDa. The mixture of cells and PGA was then buffered in citric acid, and micro-filtered using a filter with an opening of 0.16 microns.

The filtrate was neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million daltons using the method described above in conjunction with example 1.

EXAMPLE 4

PGA

Bacillus licheniformis ATCC 9945a was grown in Medium E. The fermentation was carried out at small scale, in shake flasks, at 37 C. Aeration was provided by diffusion. When the viscosity stopped rising, the pH of the fermentation broth was lowered to 2 by the addition of HCl. The cells were then removed by passing the broth through a 0.22 micron TFF filter and collecting the filtrate. The filtrate was then neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million daltons using the method described above in conjunction with example 1.

EXAMPLE 5

PGA

Bacillus licheniformis ATCC 9945a was grown in Medium E. The fermentation was carried out at small scale, in shake flasks, at 37 C. Aeration was provided by diffusion. When the viscosity stopped rising, the pH of the fermentation broth was lowered to 2 by the addition of HCl. The cells were then removed by centrifugation at a speed over 10,000×g. The supernatant was then neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million daltons using the method described above in conjunction with example 1.

What is claimed is:

1. A method for producing poly-gamma-glutamic acid (PGA), comprising:
    fermenting a *Bacillus* in a fermentation broth to allow production by the Bacillus of PGA, wherein the fermentation increases the broth viscosity;
    terminating the fermentation when the broth viscosity ceases to substantially increase;
    buffer exchanging the fermentation broth via diafiltration using a filter having a molecular weight cutoff of at least 30 kDA and less than 100 kDa;
    lowering pH of the buffer exchanged solution to about 2 or less;
    removing the *Bacillus* cells from the buffer exchanged fermented broth comprising filtering the *Bacillus* cells from the buffer exchanged fermented broth using a filter with a pore opening of about 0.22 microns or less; and
    neutralizing the pH of the resulting cell free, buffer exchanged fermentation broth.

2. The method of claim 1, wherein the *Bacillus* is a *Bacillus licheniformis*.

3. The method of claim 2, wherein the *Bacillus* is *Bacillus licheniformis* ATCC 9945a.

4. The method of claim 1, wherein the fermentation broth comprises glutamic acid, citric acid, glycerol, ammonium sulfate, dipotassium phosphate, magnesium sulfate, manganese sulfate, and calcium chloride.

5. The method of claim 1, wherein the fermentation is carried out at a temperature of about 37 C.

6. The method of claim 5, wherein the fermentation is carried out with agitation using air at a flow of about 1 reactor volume per minute.

7. The method of claim 6, wherein the fermentation is carried out in a pressurized vessel.

8. The method of claim 1, wherein the fermentation is carried out for about three to five days.

9. The method of claim 1, wherein the fermentation is terminated by decreasing the pH to about 2 or less.

10. The method of claim 1, wherein the fermentation is terminated by beginning the buffer exchange step.

11. The method of claim 1, wherein the step of adjusting the pH comprises buffering with citric acid.

12. The method of claim 1, further comprising buffer exchanging the neutralized filtrate via diafiltration using a filter with a molecular weight cutoff of less than 100 kDa.

13. The method of claim 12, wherein the diafiltration is carried out using a filter with a molecular weight cutoff of at least 30 kDa.

14. A method for producing poly-gamma-glutamic acid (PGA), comprising:
    fermenting a *Bacillus* in a fermentation broth for sufficient time to allow production by the *Bacillus* of PGA;
    terminating the fermentation when the broth viscosity ceases to substantially increase;
    buffer exchanging the fermentation broth via diafiltration using a filter with a molecular weight cutoff of at least 30 kDa and less than 100 kDa;
    lowering the pH of the buffer exchanged fermentation broth to about 2 or less;
    removing the *Bacillus* cells from the lowered-pH, buffer exchanged fermented broth comprising filtering the

*Bacillus* cells from the buffer exchanged fermented broth using a filter with a pore opening of about 0.22 microns or less;

neutralizing the pH of the cell-free buffer exchanged broth; and buffer exchanging the cell-free fermentation broth via diafiltration using a filter with a molecular weight cutoff of at least 30 kDa and less than 100 kDa to concentrate the solution.

15. The method of claim 14, wherein the fermentation is carried out in a pressurized vessel.

16. A method for producing poly-gamma-glutamic acid (PGA), comprising:

fermenting a *Bacillus licheniformis* ATCC 9945 a in a fermentation broth to allow production of by the *Bacillus* of PGA, wherein the fermentation is carried out in a pressurized vessel and the fermentation increases the broth viscosity;

terminating the fermentation when the broth viscosity ceases to substantially increase;

buffer exchanging the fermentation broth via diafiltration using a filter with a molecular weight cutoff of at least 30 kDa and less than 100 kDa;

lowering the pH of the buffer exchanged fermentation broth to about 2 or less;

filtering the *Bacillus* cells from the buffer exchanged fermented broth using a filter with a pore opening of about 0.22 microns or less; and neutralizing the pH of the resulting filtrate.

17. The method of claim 16, wherein the fermentation is carried out with agitation using air at a flow of about 1 reactor volume per minute.

18. The method of claim 16, further comprising buffer exchanging the cell-free solution via diafiltration using a filter with a molecular weight cutoff of at least 30 kDa and less than 100 kDa to concentrate the solution.

19. The method of claim 1, further comprising sterile filtering the resulting solution.

20. The method of claim 1, further comprising freeze drying the resulting PGA.

* * * * *